(12) United States Patent
Elbasiony

(10) Patent No.: US 8,831,321 B1
(45) Date of Patent: Sep. 9, 2014

(54) SIDE BRANCH DETECTION METHODS, SYSTEMS AND DEVICES

(75) Inventor: Amr Elbasiony, Chelmsford, MA (US)

(73) Assignee: Lightlab Imaging, Inc., Westford, MA (US)

( * ) Notice: Subject to any disclaimer, the term of this patent is extended or adjusted under 35 U.S.C. 154(b) by 260 days.

(21) Appl. No.: 13/340,915

(22) Filed: Dec. 30, 2011

Related U.S. Application Data

(60) Provisional application No. 61/556,515, filed on Nov. 7, 2011.

(51) Int. Cl.
*G06K 9/00* (2006.01)

(52) U.S. Cl.
USPC ............................................. 382/131

(58) Field of Classification Search
None
See application file for complete search history.

(56) References Cited

U.S. PATENT DOCUMENTS

| | | | |
|---|---|---|---|
| 5,054,492 A | 10/1991 | Scribner et al. |
| 5,321,501 A | 6/1994 | Swanson et al. |
| 5,459,570 A | 10/1995 | Swanson et al. |
| 5,465,147 A | 11/1995 | Swanson |
| 5,488,674 A | 1/1996 | Burt et al. |
| 5,509,093 A | 4/1996 | Miller et al. |
| 5,531,227 A | 7/1996 | Schneider |
| 5,619,368 A | 4/1997 | Swanson |
| 5,662,109 A | 9/1997 | Hutson |
| 5,748,598 A | 5/1998 | Swanson et al. |
| 5,771,895 A | 6/1998 | Slager |
| 5,784,352 A | 7/1998 | Swanson et al. |
| 5,797,849 A | 8/1998 | Vesely et al. |
| 5,956,355 A | 9/1999 | Swanson et al. |
| 5,989,189 A | 11/1999 | LeBlanc et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |

(Continued)

FOREIGN PATENT DOCUMENTS

| | | |
|---|---|---|
| EP | 2062526 | 5/2009 |
| WO | 2006076409 | 7/2006 |
| WO | 2007002685 | 1/2007 |

OTHER PUBLICATIONS

Unal, Gozde, et al. "Shape-driven segmentation of the arterial wall in intravascular ultrasound images." Information Technology in Biomedicine, IEEE Transactions on 12.3 (2008): 335-347.*

(Continued)

*Primary Examiner* — Nirav G Patel
(74) *Attorney, Agent, or Firm* — K&L Gates LLP

(57) ABSTRACT

In one embodiment, the invention relates to a method of detecting a side branch for a vessel scanned using a probe. The method includes storing optical coherence image data obtained during a pullback through the vessel in a memory device, the optical coherence image data comprising a plurality of frames; identifying a first region having a first intensity in a first frame of the plurality of frames; identifying a second region having a second intensity in the first frame of the plurality of frames; identifying a third region having a third intensity in the first frame of the plurality of frames; comparing the first intensity to the second intensity; comparing the third intensity to the second intensity; and generating an output characterizing the second region as a candidate side branch when the first intensity and the third intensity are both greater than the second intensity.

21 Claims, 14 Drawing Sheets

(56) References Cited

U.S. PATENT DOCUMENTS

| | | | |
|---|---|---|---|
| 6,208,883 B1 | 3/2001 | Holupka et al. | |
| 6,282,011 B1 | 8/2001 | Tearney et al. | |
| 6,381,350 B1 | 4/2002 | Klingensmith et al. | |
| 6,385,332 B1 | 5/2002 | Zahalka et al. | |
| 6,421,164 B2 | 7/2002 | Tearney et al. | |
| 6,445,939 B1 | 9/2002 | Swanson et al. | |
| 6,471,656 B1 | 10/2002 | Shalman et al. | |
| 6,485,413 B1 | 11/2002 | Boppart et al. | |
| 6,501,551 B1 | 12/2002 | Tearney et al. | |
| 6,552,796 B2 | 4/2003 | Magnin et al. | |
| 6,564,087 B1 | 5/2003 | Pitris et al. | |
| 6,570,659 B2 | 5/2003 | Schmitt | |
| 6,585,660 B2 | 7/2003 | Dorando et al. | |
| 6,697,667 B1 | 2/2004 | Lee et al. | |
| 6,706,004 B2 | 3/2004 | Tearney et al. | |
| 6,716,178 B1 | 4/2004 | Kilpatrick et al. | |
| 6,785,409 B1 | 8/2004 | Suri | |
| 6,868,736 B2 | 3/2005 | Sawatari et al. | |
| 6,879,851 B2 | 4/2005 | McNamara et al. | |
| 6,891,984 B2 | 5/2005 | Petersen et al. | |
| 6,947,040 B2 | 9/2005 | Tek et al. | |
| 7,134,994 B2 | 11/2006 | Alpert et al. | |
| 7,208,333 B2 | 4/2007 | Flanders et al. | |
| 7,231,243 B2 | 6/2007 | Tearney et al. | |
| 7,241,286 B2 | 7/2007 | Atlas | |
| 7,329,223 B1 | 2/2008 | Ainsworth et al. | |
| 7,359,554 B2 | 4/2008 | Klingensmith et al. | |
| 7,397,935 B2 | 7/2008 | Kimmel et al. | |
| 7,414,779 B2 | 8/2008 | Huber et al. | |
| 7,415,049 B2 | 8/2008 | Flanders et al. | |
| 7,450,241 B2 | 11/2008 | Zuluaga | |
| 7,532,920 B1 | 5/2009 | Ainsworth et al. | |
| 7,593,559 B2 | 9/2009 | Toth et al. | |
| 7,610,081 B2 | 10/2009 | Redel | |
| 7,625,366 B2 | 12/2009 | Atlas | |
| 7,627,156 B2 | 12/2009 | Margolis et al. | |
| 7,650,179 B2 | 1/2010 | Redel et al. | |
| 7,679,754 B2 | 3/2010 | Zuluaga | |
| 7,706,585 B2 | 4/2010 | Kleen | |
| 7,729,746 B2 | 6/2010 | Redel et al. | |
| 7,733,497 B2 | 6/2010 | Yun et al. | |
| 7,783,338 B2 | 8/2010 | Ainsworth et al. | |
| 7,785,286 B2 | 8/2010 | Magnin et al. | |
| 7,801,343 B2 | 9/2010 | Unal et al. | |
| 7,813,609 B2 | 10/2010 | Petersen et al. | |
| 7,831,078 B2 | 11/2010 | Unal et al. | |
| 7,843,976 B2 | 11/2010 | Cable et al. | |
| 7,848,791 B2 | 12/2010 | Schmitt et al. | |
| 7,872,759 B2 | 1/2011 | Tearney et al. | |
| 7,916,387 B2 | 3/2011 | Schmitt | |
| 7,930,014 B2 | 4/2011 | Huennekens et al. | |
| 7,935,060 B2 | 5/2011 | Schmitt et al. | |
| 8,029,447 B2 | 10/2011 | Kanz et al. | |
| 8,116,605 B2 | 2/2012 | Petersen et al. | |
| 8,206,377 B2 | 6/2012 | Petroff | |
| 8,208,995 B2 | 6/2012 | Tearney et al. | |
| 8,223,143 B2 | 7/2012 | Dastmalchi et al. | |
| 8,315,282 B2 | 11/2012 | Huber et al. | |
| 8,325,419 B2 | 12/2012 | Schmitt et al. | |
| 8,412,312 B2 | 4/2013 | Judell et al. | |
| 8,478,387 B2 | 7/2013 | Xu | |
| 2002/0115931 A1 | 8/2002 | Strauss et al. | |
| 2002/0161351 A1 | 10/2002 | Samson et al. | |
| 2005/0201662 A1 | 9/2005 | Petersen et al. | |
| 2005/0238067 A1 | 10/2005 | Choi | |
| 2006/0095065 A1 | 5/2006 | Tanimura et al. | |
| 2006/0135870 A1 | 6/2006 | Webler | |
| 2006/0165270 A1 | 7/2006 | Borgert et al. | |
| 2007/0060822 A1 | 3/2007 | Alpert et al. | |
| 2007/0165916 A1 | 7/2007 | Cloutier et al. | |
| 2007/0232933 A1 | 10/2007 | Gille et al. | |
| 2008/0228086 A1 | 9/2008 | Ilegbusi et al. | |
| 2008/0281205 A1 | 11/2008 | Naghavi et al. | |
| 2009/0306520 A1 | 12/2009 | Schmitt et al. | |
| 2010/0027865 A1* | 2/2010 | Wels et al. | 382/131 |
| 2010/0076320 A1 | 3/2010 | Petersen et al. | |
| 2010/0094127 A1 | 4/2010 | Xu | |
| 2010/0253949 A1 | 10/2010 | Adler et al. | |
| 2011/0071404 A1* | 3/2011 | Schmitt et al. | 600/479 |
| 2011/0071405 A1 | 3/2011 | Judell et al. | |
| 2011/0101207 A1 | 5/2011 | Schmitt | |
| 2012/0130243 A1* | 5/2012 | Balocco et al. | 600/443 |

OTHER PUBLICATIONS

Okamura, Takayuki, et al. "3-Dimensional Optical Coherence Tomography Assessment of Jailed Side Branches by Bioresorbable Vascular ScaffoldsA Proposal for Classification." JACC: Cardiovascular Interventions 3.8 (2010): 836-844.*

Briguori et al., "Intravascular ultrasound criteria for the assessment of the functional significance of intermediate coronary artery stenoses and comparison with fractional flow reserve," Am J. Cardiol 87:136-141, 2001.

Kassab et al., "The pattern of coronary arteriolar bifurcations and the uniform shear hypothesis," Annals of Biomedical Engineering 23 (1): 13-20, 1995.

Hariri et al., "An automatic image processing algorithm for initiating and terminating intracoronary OFDI pullback" Biomedical Optics Express 566 1:2 (Sep. 1, 2010).

Harrison et al., "The value of lesion cross-sectional area determined by quantitative coronary angiography in assessing the physiologic significance of proximal left anterior descending coronary arterial stenoses," Circulation 69:6 1111-1119, 1984.

Kirkeeide, "Coronary obstructions, morphology, and physiologic significance," in Reiber JHC and Serruys PW (eds.), Quantitative Coronary Arteriography, Kluwer Academic Publishers, the Netherlands, 1991, pp. 229-244.

Kolyva et al., "Increased diastolic time fraction as beneficial adjunct of α1-adrenergic receptor blockade after percutaneous coronary intervention," Am J Physiol Heart Circ Physiol 295: H2054-H2060, 2008.

Kolyva et al., "'Windkesselness' of coronary arteries hampers assessment of human coronary wave speed by single-point technique," Am J Physiol Heart Circ Physiol, 295: H482-H490, 2008.

Laslett, "Normal left main coronary artery diameter can be predicted from diameters of its branch vessels," Clinical Cardiology 18 (10): 580-582, 1995.

Ofili et al., "Differential characterization of blood flow, velocity, and vascular resistance between proximal and distal normal epicardial human coronary arteries: analysis by intracoronary Doppler spectral flow velocity," Am Heart J. 130:1 37-46, 1995.

Ohta et al., "Rheological Changes After Stenting of a Cerebral Aneurysm: A Finite Element Modeling Approach," Cardiovascular and Interventional Radiology (2005) 28:768-772.

Pijls et al., "Fractional Flow Reserve (FFR) Post-Stent Registry Investigators Coronary pressure measurement after stenting predicts adverse events at follow-up: a multicenter registry", Circulation 2002; 105:2950-2954.

Seiler et al., "Basic structure-function relations of the epicardial coronary vascular tree, Basis of quantitative coronary arteriography for diffuse coronary artery disease," Circulation 85 (6): 1987-2003, 1992.

Siebes et al., "Single-wire pressure and flow velocity measurement to quantify coronary stenosis hemodynamics and effects of percutaneous interventions," Circulation 109:756-762, 2004.

Sihan et al., "A Novel Approach to Quantitative Analysis of Intravascular Optical Coherence Tomography Imaging," Computers in Cardiology 2008; 35:1089-1092.

Sihan et al., "Fully Automatic Three-Dimensional Quantitative Analysis of Intracoronary Optical Coherence Tomography: Method and Validation," Catheterization and Cardiovascular Interventions 74:1058-1065 (2009).

Spaan, "Coronary Blood Flow," Ch 12. Dordrecht, The Netherlands: Kluwer Acedemic Publishers, Boston; 1991: pp. 333-361.

Takagi et al., "Clinical potential of intravascular ultrasound for physiological assessment of coronary stenosis," Circulation 100: 250-255, 1999.

(56) References Cited

OTHER PUBLICATIONS

Verhoeff et al., "Influence of percutaneous coronary intervention on coronary microvascular resistance index," Circulation 111:76-82, 2005.

White et al., "Does visual interpretation of the coronary arteriogram predict the physiologic importance of a coronary stenosis?," N. Engl J Med 310:13 819-824, 1984.

Wilson et al., "Prediction of the physiologic significance of coronary arterial lesions by quantitative lesion geometry in patients with limited coronary artery disease," Circulation 75: p. 723 (1987).

PCT International Search Report and Written Opinion of International Searching Authority for International Patent Application No. PCT/US2010/049887, mailed Jun. 9, 2011, 19 pages.

Herrington et al., "Semi-automated boundary detection for intravascular ultrasound," Computers in Cardiology 1992 Proceedings., pp. 103-106, Oct. 1992.

Sonka et al., "Segmentation of intravascular ultrasound images: a knowledge-based approach," IEEE Transactions on Medical Imaging, 14(4):719-732, Dec. 1995.

Mojsilovic et al., "Automatic segmentation of intravascular ultrasound images: A textrue-based approach," Annals of Biomedical Engineering, 25:1059-1071, Nov. 1997.

Gil et al., "Automatic segmentation of artery wall in coronary IVUS images: a probabilistic approach," Computers in Cardiology 2000; 27:687-690.

Haas et al., "Segmentation of 3D intravascular ultrasonic images based on a random field model," Ultrasound in Medicine & Biology, 26:2, 297-306, 2000.

Kovalski et al., "Three-dimensional automatic quantitative analysis of intravascular ultrasound images," Ultrasound in Medicine & Biology, 26(4):527-537, 2000.

Pujol et al., "Intravascular Ultrasound Images Vessel Characterization using AdaBoost," Functional Imaging and Modeling of the Heart: Lecture Notes in Computer Science, pp. 242-251, 2003.

Taki et al., "Automatic segmentation of calcified plaques and vessel borders in IVUS images," International Journal of Computer Assisted Radiology and Surgery, 3(3-4):347-354, Sep. 2008.

van den Berg et al., "Using three-dimensional rotational angiography for sizing of covered stents," Am. J. Roentgenology, 178:149-152 (2002).

Wong et al., "A novel method of coronary stent sizing using intravascular ultrasound: safety and clinical outcomes," Int. J. Angiol. , 18(1): 22-24 2009.

Bonnema et al., "An automatic algorithm for detecting stent endothelialization from volumetric optical coherence tomography datasets", Physics in Medicine and Biology, 53:12, Jun. 21, 2008, pp. 3083-3098.

Unal et al., "Stent implant follow-up in intravascular optical coherence tomography images," Int J Cardiovasc Imaging, DOI 10.1007/s10554-009-9508-4, published online Sep. 24, 2009, 8 pgs.

Xu et al., "Characterization of atherosclerosis plaques by measuring both backscattering and attenuation coefficients in optical coherence tomography," Journal of Biomedical Optics, 13:3, May/Jun. 2008, 8 pgs.

Takano et al.. "Evaluation by Optical Coherence Tomography of Neointimal Coverage of Sirolimus-Eiuting Stent Three Months After Implantation," American Journal of Cardiology, 99:8, Apr. 14, 2007, pp. 1033-1038.

Unal, et al., "Shape-Driven Segmentation of the Arterial Wall in Intravascular Ultrasound Images," Information Technology in Biomedicine, IEEE Transactions, 12:03, pp. 335-347, May 2008.

\* cited by examiner

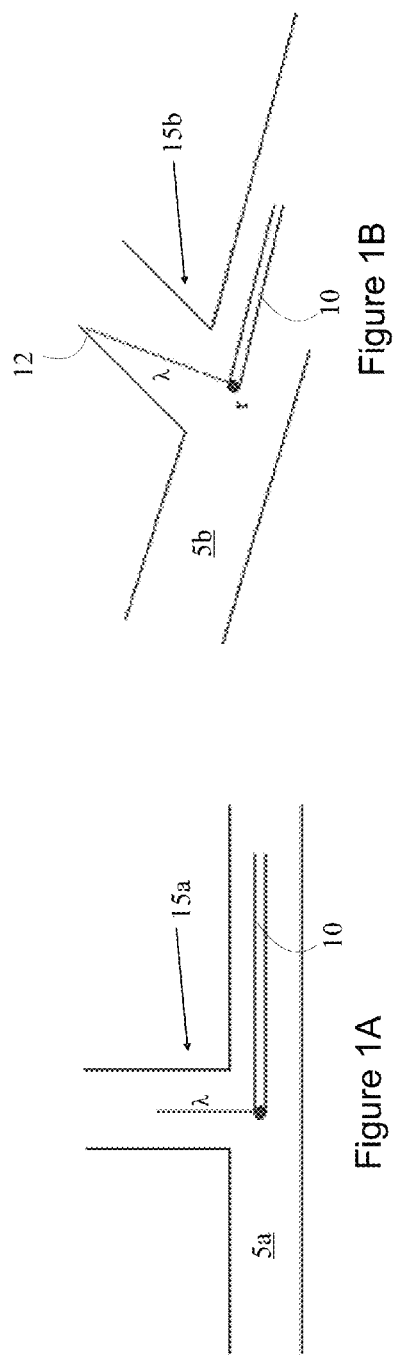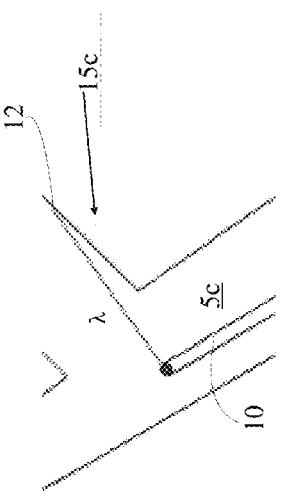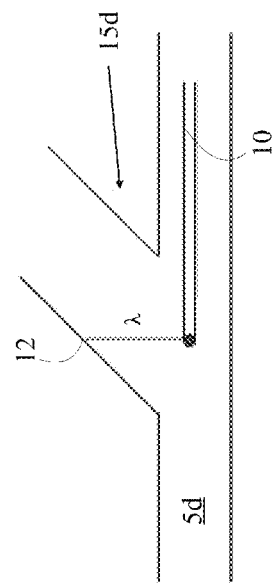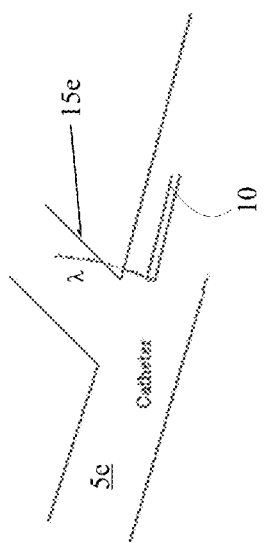

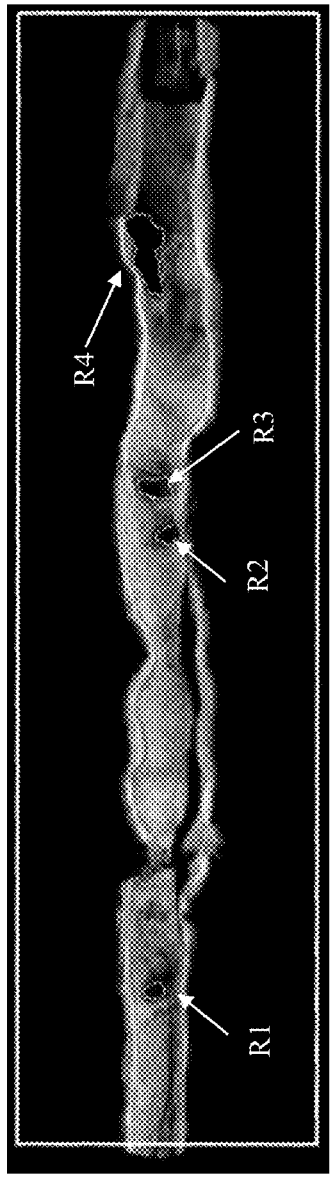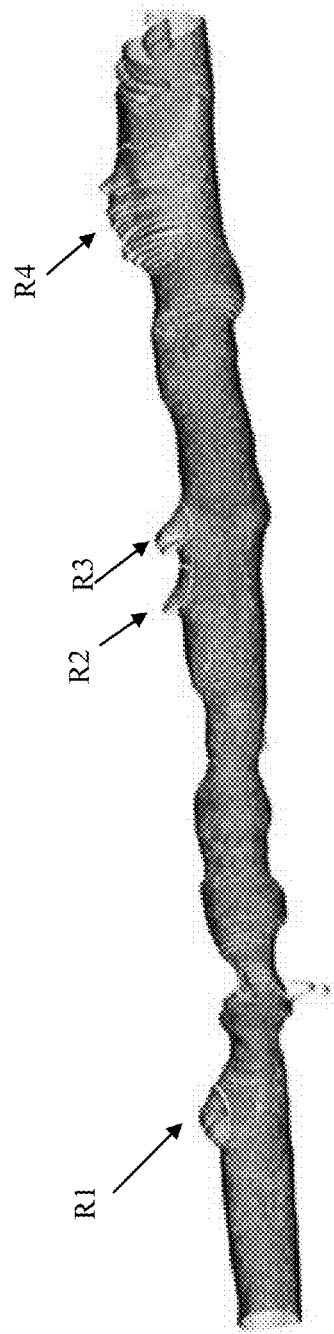
Figure 2A
Figure 2B

SIDE BRANCH DETECTION METHODS, SYSTEMS AND DEVICES

CROSS REFERENCE TO RELATED APPLICATIONS

This application claims priority to and the benefit of U.S. Provisional Patent Application No. 61/556,515, filed on Nov. 7, 2011, the disclosure of which is herein incorporated by reference in its entirety.

FIELD OF THE INVENTION

The invention relates generally to devices and methods suitable for use in the fields of medical treatment and diagnostics and more specifically to devices and methods that support sensing and identifying a wall of a blood vessel, including branches, junctions or other sections or features thereof.

BACKGROUND

Coronary artery disease is one of the leading causes of death worldwide. The ability to better diagnose, monitor, and treat coronary artery diseases can be of life saving importance. Intravascular optical coherence tomography (OCT) is a catheter-based imaging modality that uses light to peer into coronary artery walls and present images valuable for the study of the vascular wall architecture. Utilizing coherent light, interferometry, and micro-optics, OCT can provide video-rate in-vivo tomography within a diseased vessel with micrometer level resolution. This level of detail made possible with OCT allows a clinician to diagnose as well as monitor the progression of coronary artery disease.

The quantitative assessment of vascular pathology and its progression involves the calculation of different quantitative measures such as pressure drops which can rely on the accurate identification of fluid flow and geometry of the lumen, including side branch geometry. Side branches extending from a lumen in OCT images are often not easily identified. In part, this results because side branches can be obscured by the guide wire used in various OCT probes or otherwise obscured by stent struts, blood, and shadows. Shadows and other imaging data artifacts can be challenging to resolve and eliminate. As a result, important landmarks along the length of an artery such as side branches can be mistaken for tissue or simply not identified. Given that placing a stent over a side branch can be damaging or even fatal for a patient and that certain pressure calculations require side branch data to be accurate, there is a need for a reliable technique that can identify side branches.

The present invention addresses these needs and others.

SUMMARY

In part, the invention relates to methods, systems and components thereof suitable for more accurately identifying and quantifying a lumen by identifying candidate or potential side branches from an OCT image dataset thereof. In one embodiment, a side branch can be evaluated as a two-dimensional cross-section. Multiple cross-sections can be evaluated relative to each other to confirm whether a given candidate is actually a side branch or a stent or a shadow. Typically, such a cross-section of a vessel can exhibit a pattern of a high intensity region associated with tissue, followed by a low intensity region in the sector of the vessel in which the side branch occurs, and then again followed by a high intensity region associated with the tissue on the other edge of the side branch.

Given this pattern and other similar patterns, image processing techniques can be used to track such patterns and identify candidate side branches. Once the candidate side branches are identified, information such as changes in the size or angular position of a shadow region between adjacent frames or cross-sectional data sets of a given vessel, the intensity profiles from stents, guide wire shadow analysis, methods of compensating for blood disposed in the vessel, and other techniques can be used to accept or reject the candidates such that one or more side branches can be identified.

In one embodiment, the methods and software modules described herein are configured to have sufficient sensitivity and reliability by using the geometric, thickness, and other features of side branches and blood detection within an image as well as across a series of images.

Several important treatment decisions depend on the localization of side branches in a given pullback, for instance, a physician may fine tune his/her choice of the position and length of a stent based on the location of side branches. In addition, the detection of artery wall and stent struts can be further improved by the automatic detection of side branches. Furthermore, calculating the blood flow or a pressure change in a given vessel can benefit from data relating to side branch detection and positioning. One or more embodiments of the invention relate to automatic side branch detection methods and systems that facilitate these objectives.

In one embodiment, the invention relates to a method of detecting a side branch for a vessel scanned using an imaging probe. The method includes storing image data obtained during a pullback through the vessel in a memory device, the image data comprising a plurality of frames; identifying a first region having a first intensity in a first frame of the plurality of frames; identifying a second region having a second intensity in the first frame of the plurality of frames; identifying a third region having a third intensity in the first frame of the plurality of frames; comparing the first intensity to the second intensity; comparing the third intensity to the second intensity; and generating an output characterizing the second region as a candidate side branch when the first intensity and the third intensity are both greater than the second intensity.

In one embodiment, the second region has a first angular position and the method further includes the step of determining if a shadow region having a second angular position substantially the same as the first angular position is present in a second frame adjacent to the first frame. The first intensity and the third intensity can be substantially equal. The first region and the third region can be separated by a gap which at least partially defines the second region. The method can further include the step of applying a binary image mask such that each of the first intensity, the second intensity, and the third intensity are characterized as foreground data or background data in response to their respective intensities. The method can further include the step of fitting an ellipse between at least two of the first, second, and third regions and excluding at least one additional region disposed in the ellipse having a fourth intensity greater than the second intensity. The image data can be optical coherence tomography image data or IVUS data and further include the step of determining if the second region is a side branch using optical coherence tomography image data or IVUS data from one or more adjacent frames.

In one embodiment, the second region can have a first angular position and the method can further include the step of determining if a shadow region having a second angular position substantially the same as the first angular position is present in a second frame adjacent to the first frame. In one embodiment, the image data is optical coherence tomography image data and the imaging probe is an optical coherence tomography probe.

The method can further include the step of detecting a guide wire in the first frame and determining that the second region is a side branch if the guide wire has a shadow profile that exceeds a predetermined shadow profile threshold. The method of can further include the steps of building a computer-based tree using a plurality of midpoints of detected shadow regions and pruning the tree to determine if the second region is an outlier or a side branch. In one embodiment, the outlier is selected from the group consisting of a shadow, blood, thin tissue, a stent, and an imaging artifact.

In one embodiment, the invention relates to an automatic processor-based system for detecting a side branch of a vessel. The system includes a memory; and a processor in communication with the memory, wherein the memory comprises instructions executable by the processor to cause the processor to: determine an average intensity for each scan line in a first frame of optical coherence tomography image data; identify the scan lines having an average intensity greater than a threshold as vessel data; identify the scan lines having an average intensity less than the threshold as outlier data; and identify a first scan line and a second scan line such that the first scan line and the second scan line are not adjacent; and determine a region between the first scan line and the second line is an outlier.

In one embodiment, the outlier is selected from the group consisting of a side branch, shadow, blood, thin tissue, a stent, and an imaging artifact. The memory can further include instructions executable by the processor to cause the processor to: determine that the first scan line is adjacent to a third scan line from the vessel data and a fourth scan line from the outlier data; and determine that the second scan line is adjacent to a fifth scan line from the vessel data and a sixth scan line from the outlier data. The threshold can be derived from a foreground intensity. The threshold can be a percentage of a foreground intensity.

In one embodiment, the invention relates to a method of detecting a side branch of a vessel scanned using an optical coherence tomography probe. The method includes storing optical coherence image data obtained during a pullback through the vessel in a memory device, the optical coherence image data comprising a plurality of frames; generating a first set of candidate side branches based on intensity variations on a per frame basis, each candidate side branch having a corresponding shadow region; comparing a position of each shadow region to another shadow region in an adjacent frame; and generating a first subset of candidate side branches having a cardinality that is less than that of the set of candidate side branches.

In one embodiment, the method can further include the steps of detecting a guide wire in one or more frames and generating a second subset having a cardinality that is less than that of the first subset if the guide wire has a shadow profile that exceeds a predetermined shadow profile threshold.

The method can further include the step of applying an image mask such that intensity variations are characterized as foreground data or background data in response to their respective intensities. The method can further include the step of generating an output characterizing a region in a frame as a candidate side branch when a first intensity at a first position and a third intensity at a third position are both greater than a second intensity in the region. The method can further include the step of removing imaging artifacts using a tissue thickness threshold. The method can further include the step of displaying a cross-sectional image of the vessel wherein one or more side branches are identified.

Notwithstanding the foregoing, while embodiments of the invention are described in the context of OCT images, the present invention is not so limited. Thus, for example, identifying any side branch in any vascular image, such as an ultrasound or IVUS image, a co-registered image, such as OCT and IVUS, or other imaging modality is within the spirit and scope of the invention.

This Summary is provided merely to introduce certain concepts and not to identify any key or essential features of the claimed subject matter.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

FIGS. 1A-1E show schematic diagrams of an OCT probe in a lumen positioned relative to a side branch in accordance with an illustrative embodiment of the invention.

FIGS. 2A and 2B show perspective views of a three-dimensional image of a lumen having side branches generated using OCT image data in accordance with an illustrative embodiment of the invention.

DETAILED DESCRIPTION

Figure 3A:
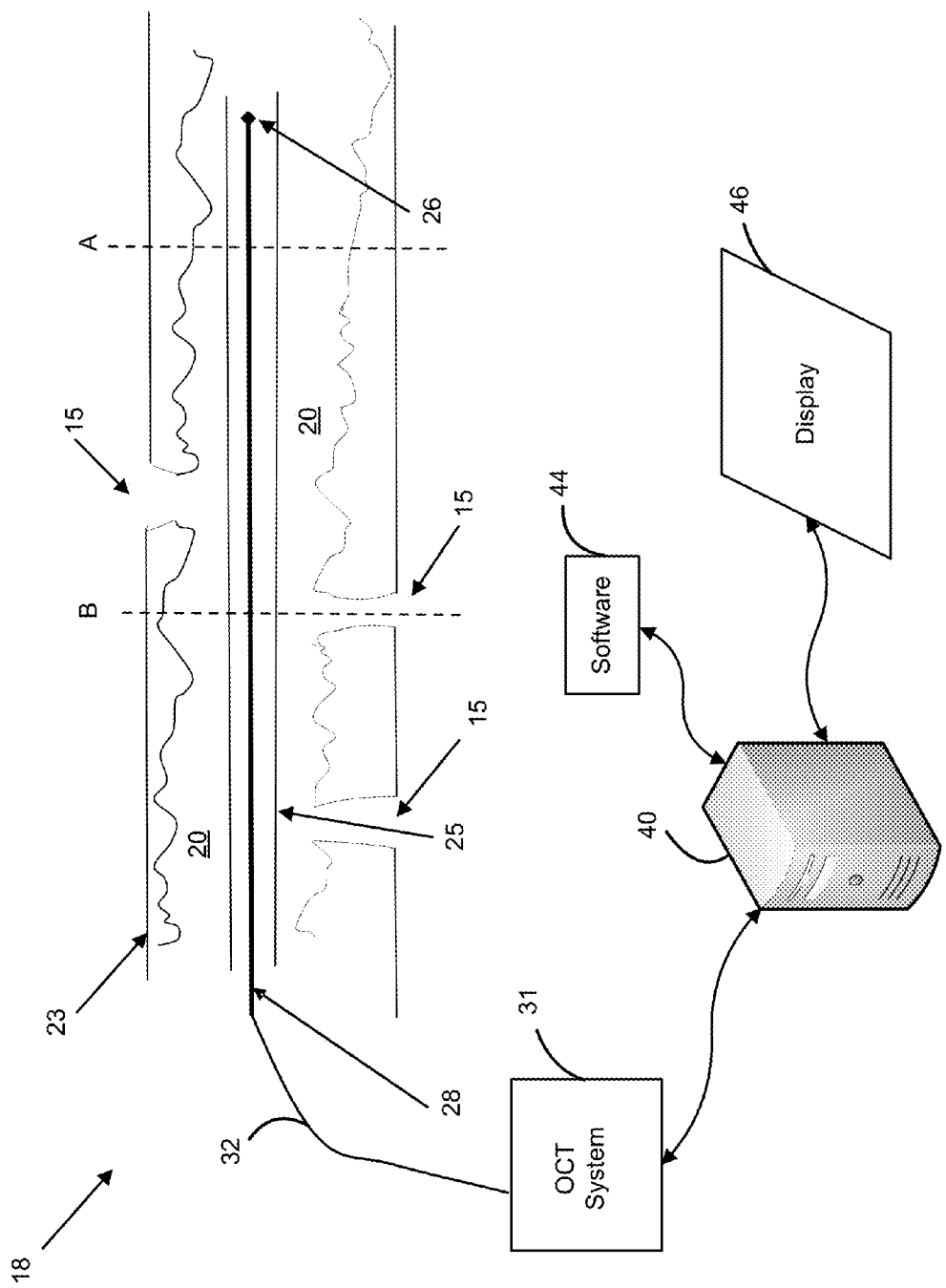
FIG. 3A is a schematic diagram showing an OCT system having a probe and other components configured to collect data from a vessel and to detect the side branches in accordance with an illustrative embodiment of the invention.

In part, the invention relates to improving the identification and segmentation of a lumen in an intravascular image of a vessel of interest by detecting side branches therein. One example of a vessel of interest is a human artery. An arterial wall defines a lumen in which blood flows such that the artery is in fluid communication with the heart. The artery is an elongate tube having various openings defined by the arterial wall. The openings connect to other branches or side branches of the artery of interest. The branches themselves have lumens defined by walls of the artery or other vessels.

Several important treatment decisions depend on the localization of side branches in a given pullback. For instance, the physician or other operator may fine tune his/her choice of the position and length of a stent based on the location of side branches. In addition, the detection of artery wall and stent struts can be further improved by the automatic detection of side branches. Furthermore, the ability to accurately calculate the blood flow in a given vessel benefits from and may require reliable side branch detection for a given implementation.

An optical coherence tomography (OCT) probe can be disposed in a given lumen and moved to collect data with respect to the walls defining the lumen and various substructures or openings in such walls that connect to or open to define side branches. FIGS. 1A-1E show various lumens $5a$, $5b$, $5c$, $5d$, and $5e$ (generally referred to as a lumen 5) having an OCT probe 10 disposed therein and respective side branches $15a$, $15b$, $15c$, $15d$, and $15e$ (generally referred to as a side branch 15). The probe 10 emits light X and receives light scattered from the tissue it encounters. When travelling along an artery, such as during a pullback as described below, an opening or depression in the sidewall can be another branch of the artery or a branch of another vessel.

In FIG. 1A, light may not be received at a detectable level by the probe 10 due to absence of reflecting tissues in the side branch opening depending on the depth and geometry of the side branch. However, as the edges of the side branch are scanned this pattern of light, then dark, and then light can be used as a way to identify a side branch. The walls 12 of lumen for a side branch $15a$ receive and scatter light as shown in FIGS. 1B-1E. These side branches are important to detect because knowing where the side branches are helps ensure that a stent or a balloon will not be inadvertently placed or inflated in such a region.

In FIG. 1E, light from the probe 10 penetrates a thin portion of the vessel wall and continues on relative to a side branch $15e$. In this scenario, a closed vessel wall will be generated using one of the computer-based methods described herein and a data artifact such as an image segment or artifact associated with the portion of the side branch will be shown outside the vessel wall. The method and operational states of the side branch module can be configured to ignore the side branch data collected in such a scenario.

The probe 10 is typically implemented using a catheter. The catheter is introduced into a lumen of interest. The probe can include a rotating or slidable fiber that directs light λ forward into the lumen or at a direction perpendicular to the longitudinal axis of the fiber. As a result, in the case of light that is directed from the side of the fiber as the fiber rotates, OCT data is collected with respect to the walls of a lumen. The probe can include other imaging modalities in addition to OCT such as ultrasound in one embodiment.

Further, as the optical fiber is retracted (pulled-back) along the length of the vessel, a plurality of scans or OCT data sets are collected as the fiber rotates. This is referred to herein as a pullback. These data sets can be used to identify regions of interest such as locations that include a plaque for stenting or applying a balloon to open the vessel or side branches. Identifying the side branches relative to blood, shadows, and stents is also important because various pressure dependent measurements such as fractional flow reserve can be rendered more accurate with better details on how side branches change flow and pressure in a given vessel.

Figure 5A:
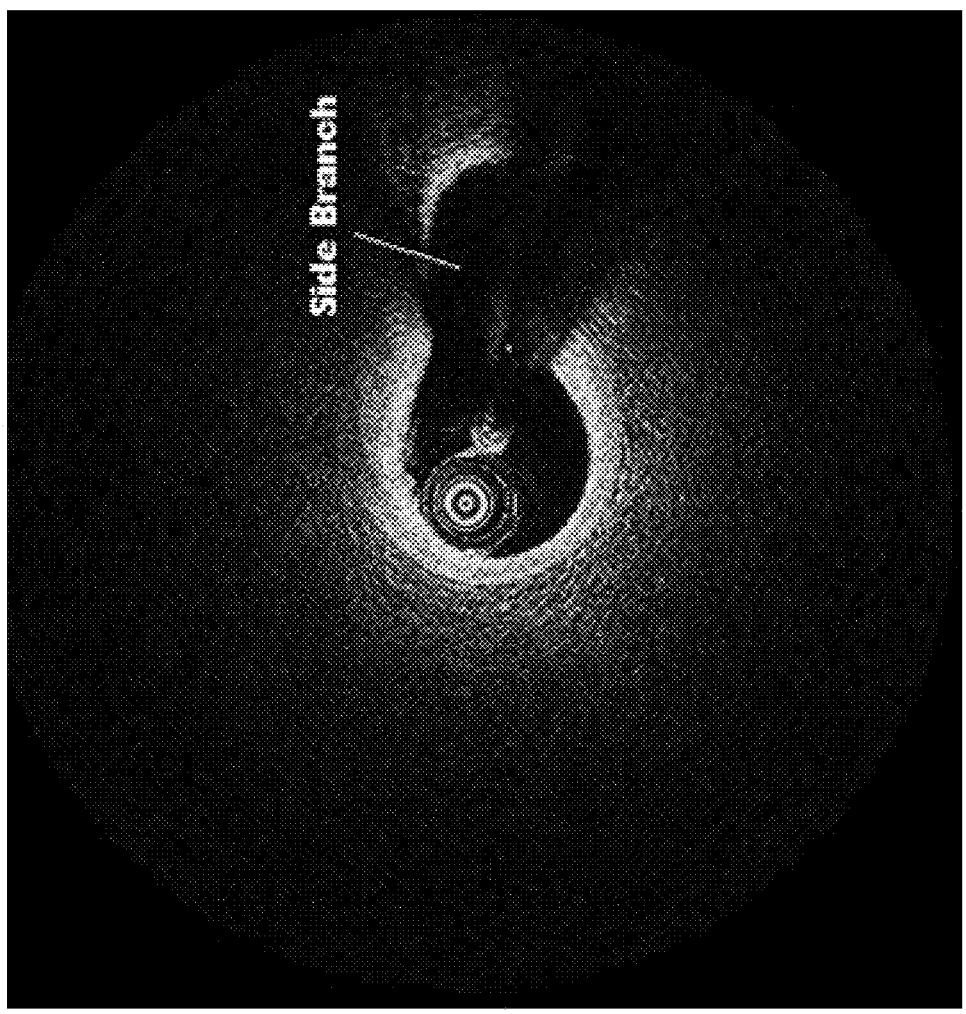
FIGS. 5A-5C show various diagrams obtained with respect to a vessel having one or more side branches using an OCT system suitable in accordance with an illustrative embodiment of the invention.

A three-dimensional image or a two dimensional cross-section of a given vessel can be generated using the OCT data collected using a probe 10 and one or more associated OCT subsystems or components. Examples of three-dimensional tomographic images of an artery generated are shown in FIGS. 2A and 2B. These images show regions R1-R4 that correspond to side branches. FIG. 5A shows a two-dimensional cross-section of a vessel having a side branch. Each figure has been processed using an image data processing pipeline and a side branch detection module or stage as described below.

Side branch detection can use various image data processing techniques and compensation schemes. This follows because there are several data collection scenarios that can occur as shown in FIGS. 1A-1E. Specifically, an OCT probe having a substantially constant imaging beam angle originating from the probe tip and four different vessel configurations are shown in these figures. The probe tip can be forward scanning or side scanning in various embodiments. Typically, beam directors such as lenses or reflectors or combinations thereof are part of the probe and used to direct the beam on to the vessel wall. The beam directors also collect the scattered light that returns from the vessel wall. As a result, distance from the vessel wall and the depth of a side branch change the intensity of the scattered light received by the probe.

In FIG. 1A, the side branch receives the imaging light from the probe 10, but it passes into the lumen of the side branch $15a$ and is not scattered back to the probe 10 or only scattered back to a reduced degree. In FIGS. 1B-1E, the light is back scattered to the probe 10, but over varying distances and from different angles based on the geometry of the side branches $15b$-$15e$ such as the angle it forms with lumens $5b$-$5e$ and the shape of its walls. These geometric variations in side branches and the exemplary side branch imaging scenarios shown in FIGS. 1A-1E, in which light does not return or returns in a manner that differs relative to the vessel wall, can be addressed using one or more embodiments described herein. These embodiments include software-based methods to automatically detect side branches that are configured to account for various scenarios associated with side branch variation and probe position. For example, the data collected in FIG. 1E can be excluded relative to the side branch $15e$ given that the vessel wall is closed at the cross-section in which the OCT data is obtained. If this data were to be used, it can cause the location of the side branch shown to be misidentified or for an extra side branch to be identified or other unwanted effects.

FIG. 3A is a high level schematic diagram depicting components of an OCT system 18 suitable for performing side branch detection, lumen detection, guide wire detection and various other processes. The OCT system 18 can include any suitable light source that satisfies the coherence and bandwidth requirements of the applications and data collection described herein. FIG. 3A is highly generalized and not to scale. A vessel or lumen of interest 20 having a vessel wall 23 is imaged using catheter 25 having a catheter portion having an optical fiber-based imaging probe 28 disposed therein. The probe 28 includes a beam director 26. The catheter 25 can include a flushing system (not shown) configured to displace a sufficient amount of blood such that in vivo OCT data collection can proceed using the probe 28. The system 18 includes an OCT system or subsystem 31 that connects to the imaging probe 28 via an optical fiber 32. The OCT system or subsystem 31 that can include a light source such as a laser, an interferometer, various optical paths, a clock generator, photodiodes, and other OCT system components.

A computer or processor can be part of the OCT system 31 or can be included as a separate subsystem 40 in electrical or optical communication with the OCT system 31. The computer or processor 40 can include memory, storage, buses and other components suitable for processing data and software configured for side branch detection and pullback data collection as discussed below. In one embodiment, the computer or processor includes software implementations or programs 44, such as a side branch detection module, a guide wire detection module, a lumen detection module, a median mask clearing module, an intensity averaging module, and other components of an image data processing pipeline or any of the methods described herein that are stored in memory and executed using a processor or other integrated circuit. A display 46 can also be part of the overall system 18 for showing cross-sectional scan data, longitudinal scans, diameter graphs, image masks, shadow regions, and other images or representations of a vessel or suitable formats. The software or programs 44 can also be configured to identify side branches such as with text, arrows, color coding, highlighting, contour lines, or other suitable human or machine readable indicia.

Cross-sectional data can be captured along the length of the lumen 20 such as at sections A and B. A total of three side branches 15 are shown in FIG. 3A. In cross-section A, no side branch is present, while in cross-section B a side branch is present. For this cross-section B of the lumen 20, the presence of a side branch will change the intensity profile for the scan lines generated using light entering the side branch and received or not received by the probe 26. Since the OCT probe 26 rotates, the cross-section at position B will include multiple C-shaped images in which the opening of the C is a shadow region associated with the side branch and the rest of the C shape corresponds to the vessel wall. An actual cross-sectional image of this type of shape is shown in FIG. 5A. The side branch portion of the OCT image can be stored as a sector associated with the ellipse or circular shape of the vessel wall in polar, Cartesian, cylindrical, or other coordinate systems.

In one embodiment, a first scan line is used to indicate the start of the side branch and a second scan line is used to indicate the end of the side branch. The side branch can also be defined by this set of scan lines that have an intensity profile that is less than the intensity of the vessel wall. The cross-sections that span each side branch, such as for example to the left and right of line B, will each experience intensity changes in a subset of their scan lines. The intensity variations for such cross-sections will diminish as the probe is pulled back such that frames of image data include less and less of the side branch and then only include the vessel wall until the next side branch is encountered. However, unlike a strut which can twist or jump between frames, the angular position of the shadow region associated with a side branch can be used to validate that a shadow region is actually a side branch that spans multiple frames such as the branch shown along cross-section B. Thus, for cross-sectional images for frames adjacent to cross-section B, on either side, a shadow region will be at about the same angular position for all three cross-sections.

Figure 3B:
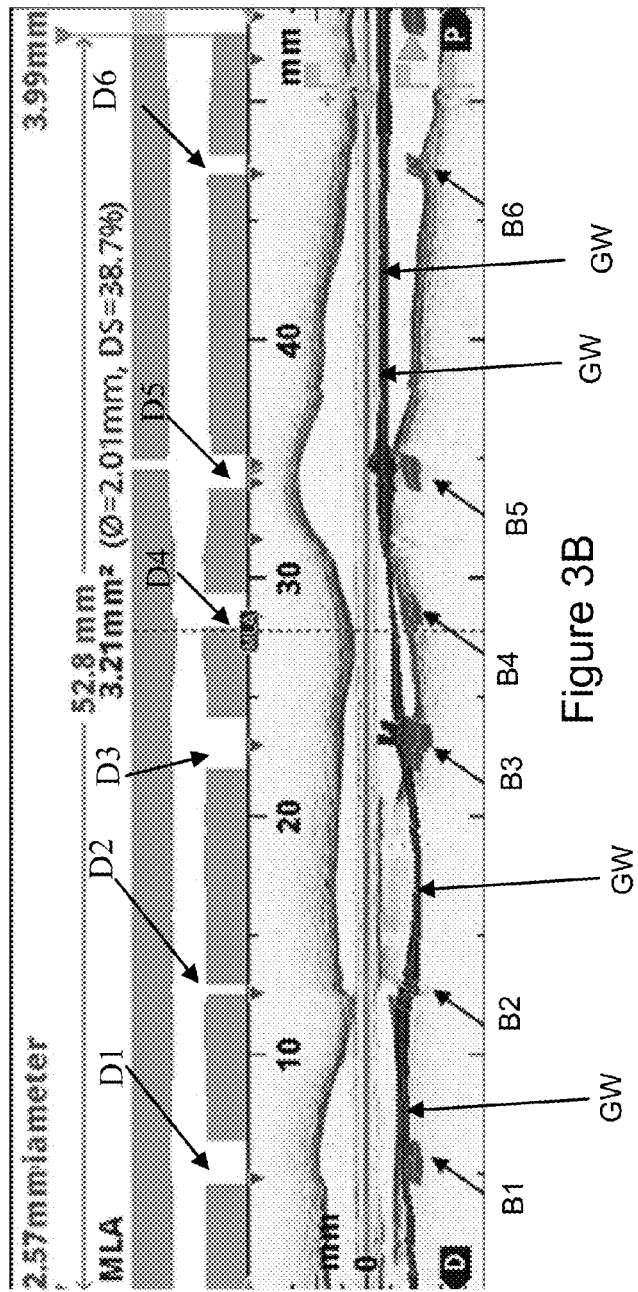
FIG. 3B shows a longitudinal cross-sectional image of a vessel having side branches and a diameter graph identifying such side branches in accordance with an illustrative embodiment of the invention.

FIG. 3B is an exemplary display of an image of a longitudinal cross-section of an artery obtained as part of an OCT pull back with a probe such as shown in FIG. 3A set below a graph depicting a mean diameter of the lumen calculated from measurements taken by the OCT system. This image is of the type that can be output to a user on a display 46 and interacted with using a mouse, keyboard, or similar input device. In one embodiment, such an image showing a longitudinal cross-sectional image along the length of a vessel or other sample of interest is referred to as the L-Mode. The arrows indicate positions where side branches B1-B6 have been identified in the bottom half of the figure. The top half of FIG. 3B shows a graph depicting a mean diameter of the lumen with cut-outs D1-D6 representing the size and location of the side branches B1-B6. The locations of the mean diameters of the lumen and size and locations of the side branches on the top graph are aligned to their actual locations on the vessel as shown in the image located below.

Still referring to FIG. 3B, the line GW on the bottom half of the figure, the L-Mode, shows the result of the guide wire detection. The guide wire GW is used to introduce and position the catheter having the optical fiber probe. The thickness of the line GW at each frame corresponds to the detected width of the guide wire shadow at the given frame. The shape of the line GW corresponds to the relative angular position (change in the angular position) of the detected guide wire shadow from one frame to the next. The side branches B1-B6, detected using the side branch detection module, are indicated in the L-Mode with blobs. The width of each blob at any given frame corresponds to the detected side branch width at the frame. The shape of the blob corresponds to the relative angular position (change in the angular position) of the detected side branch from one frame to the next. These and other graphical representations can be used in various embodiments.

Figure 4A:
FIG. 4A shows a schematic diagram of an image data processing pipeline in accordance with an illustrative embodiment of the invention.

In FIG. 4A, a high level of overview of an image data processing pipeline is shown. In one embodiment, raw image data is generated from the data collected from an interferometer in optical communication with an OCT probe. The data can be collected using a detector such as a photoreceiver. The image data processing pipeline includes various processing stages or modules that operate on the image data to accomplish a particular objective. In one embodiment, side branch detection is implemented as such a stage or module in the image data processing pipeline.

As shown in the exemplary image data processing pipeline of FIG. 4A, the pipeline includes a pipeline source and pre-modules. The pipeline source receives data from an OCT system that includes distance information relative to a sample of interest such as depth measurements along the wall of an artery. The pipeline can also include various pre-processing modules such as formatting or noise correcting modules or other filters. The pipeline source and the pre-processing modules are upstream of the three modules or stages shown. In contrast, the pipeline sink and the post-processing modules are downstream of the three modules or stages shown. The pipeline sink can include an output module configured to display images on a monitor or other device. The modules or stages shown include guide wire detection, side branch detection, and lumen detection. Although this order is preferred in one embodiment, other orders are possible, and the modules and stages can be combined or divided into different software-based modules, stages or applications. Prior to considering each stage in more detail, it is useful to consider some of the characteristics of data collected with an OCT system.

In one embodiment of the invention, the smallest data unit in an OCT image is called a sample. Further, a sequence of samples along a ray originating at the probe center to the maximum imaging depth is called a scan line. An OCT image is typically acquired one scan line at a time. Each scan line is a collection of points. A cross-sectional image can be formed from a set of scan lines collected as the probe rotates. Further, to image a segment of an artery or other vessel, the catheter is moved longitudinally while rotating. In this way, the probe acquires a set of cross-sectional images in a spiral pattern. The images originate from the various scan lines associated with a slice of the vessel or artery of interest. The image can be displayed as cross-sections, such as in FIG. 5A or they can be displayed as longitudinal sections, such as the L-mode of FIG. 3B. The combination of cross-sectional images allow a tomographic image such as the three-dimensional perspective views of a vessel in FIGS. 2A and 2B to be automatically generated using software that operates on or otherwise transforms the OCT data acquired during a pullback.

In one embodiment, the modules shown in FIG. 4A are configured to operate automatically on the image data. In one embodiment, the term "automatically" means without human intervention. Notwithstanding the foregoing, the scope of the terms discussed herein is not intended to be limiting, but rather to clarify their usage and incorporate the broadest meaning of the terms as known to those of ordinary skill in the art.

A cross-sectional image is created for each complete turn of the catheter. As part of the side branch detection module or stage of FIG. 4A, the image data is processed using one or modules in the pipeline. In one embodiment, the data associated with a given cross-section is processed as a set of data. In other embodiments, the data can be processed in other batches, data sets, or in the aggregate. Given that each cross-section continues geometric relationships between the walls of a vessel and side branches, lumen detection and side branch detection are suitable for processing data frames on a per cross-section basis. This can be seen in FIG. 3A at section B and in FIGS. 2A, 2B and others.

For example, in FIG. 2A four regions have borders that have been highlighted using a processing module of the pipeline. These four regions R1-R4 increase in size from left to right and represent four side branches. The branches themselves are not shown, but only the regions R1-R4 that correspond to the opening of the side branch in the main vessel that was imaged. In FIG. 2B, projections of the vessel wall are shown as extending from the same four side branches at regions R1-R4. These regions and side branches can be highlighted, textured or otherwise identified using any suitable designator or graphic element.

Figure 4B:
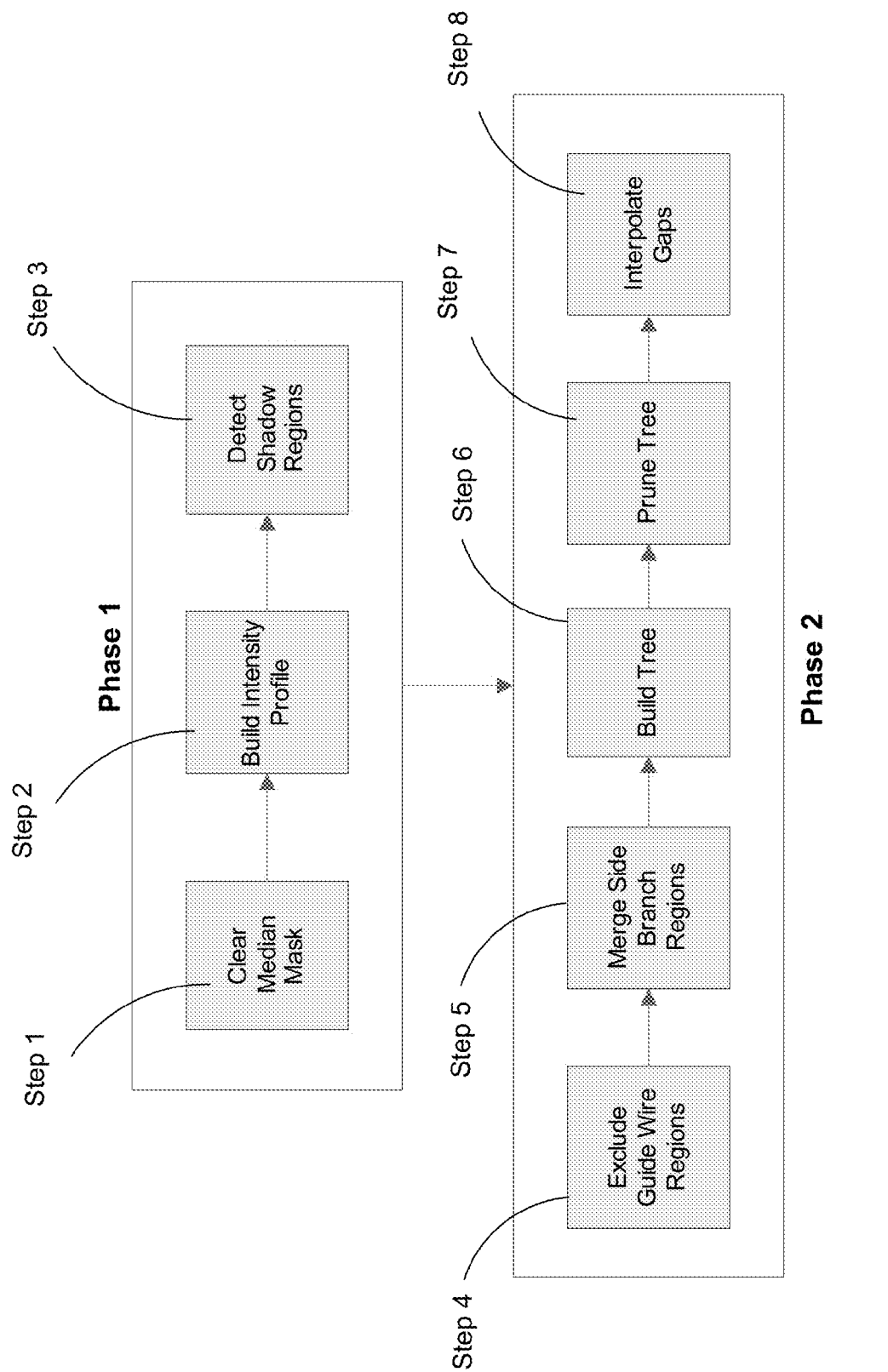
FIG. 4B shows an exemplary process suitable for implementing a side branch detection module or stage in accordance with an illustrative embodiment of the invention.

A side branch detection stage or module can be implemented in software and executes in memory on a computer or a processor such as an application specific integrated circuit. Side branch detection can be implemented using various processes or steps that execute as an algorithm. As illustrated in FIG. 4B, one embodiment of the side branch detection module or algorithm is implemented in two phases, a first phase and a second phase. The first phase performs several single frame processing functions on each individual frame in a given pullback. Each frame corresponds to the image data associated with one cross-sectional slice of the vessel. The second phase extends the first phase results with cross-frame analysis. These two phases are typically performed in the order specified in FIG. 4B.

Phase 1 of Side Branch Detection Embodiment

Single frame processing occurs during the first phase of the side branch detection algorithm. As shown in FIG. 4B, phase 1 can include the step of clearing a median mask Step 1, building an intensity profile Step 2 and detecting shadow regions Step 3. The steps can be performed in a different order and with additional or fewer steps. Additional details relating to clearing a median mask are described below with respect to FIG. 7. Prior to discussing that step, it is useful to consider the use of masks and other image processing features of the side branch detection module.

In one embodiment of the side branch detection module, a binary image mask is used. The binary image mask is "binary" in the sense that it divides the image data in to a first set and a second set. In one embodiment, the first set is the foreground data and the second set is the background data or vice versa. Other types of masks or data filtering approaches can be used. The mask can be created by processing the image data on a per frame basis or any other suitable basis. A suitable threshold is applied to the image data to create a binary foreground/background image mask. The threshold, foreground and background can be set using intensity levels or other parameters. The foreground is defined or configured to contain the potentially relevant image information (e.g. the vessel wall). In turn, the background is defined or configured to represent the empty luminal space between the catheter and vessel wall. The background portion of the mask can also be defined or configured to include a 'noise' floor' beyond the deepest imaging depth within the vessel wall.

Figure 5B:
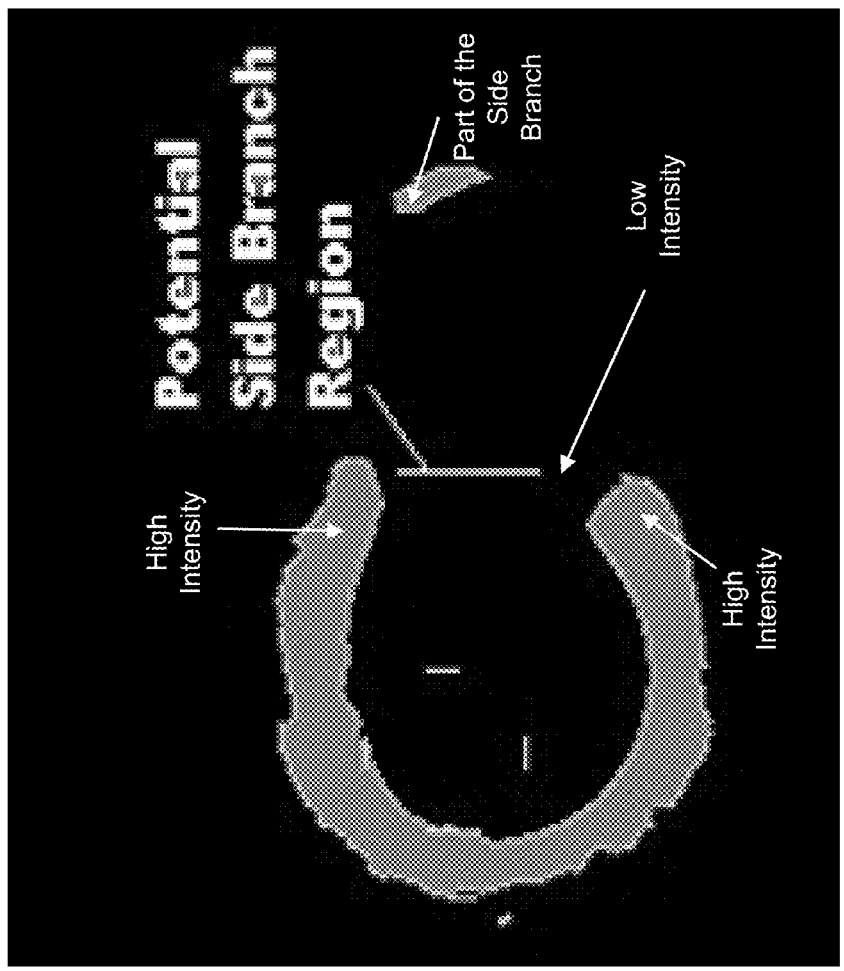

In the binary mask, a low intensity region will appear as a background (opening) in the mask image as shown in FIG. 5B while the high intensity region will appear as the foreground (vessel wall). If blood is disposed in the interior of the vessel, the OCT probe data associated with light scattered from the blood field causes the blood to be processed as tissue which causes it to appear as part of the foreground or vessel wall. As a result, if a side branch is present and blood is present, the blood can be imaged and processed as tissue which can have the undesirable consequence of filling the side branch portion of the image with a foreground signal. To remove these and similar types of artifacts, an additional processing step or steps can be used to clear the median mask.

The step of clearing the median mask or binary mask refers to identifying the geometric boundary of a vessel wall and erasing or blanking data within that boundary, such as blood, that appears to be part of the foreground. This allows a binary image mask to be formed suitable for building an intensity profile Step 2. Specifically, it allows blood to be factored out of the image data or compensated before the final binary image mask is prepared. As a result, the higher intensity light scattered from the blood does not effectively make the side branch appear as a continuous portion of the vessel wall. Additional details with respect to this mask clearing process are described in FIG. 7.

Figure 5C:
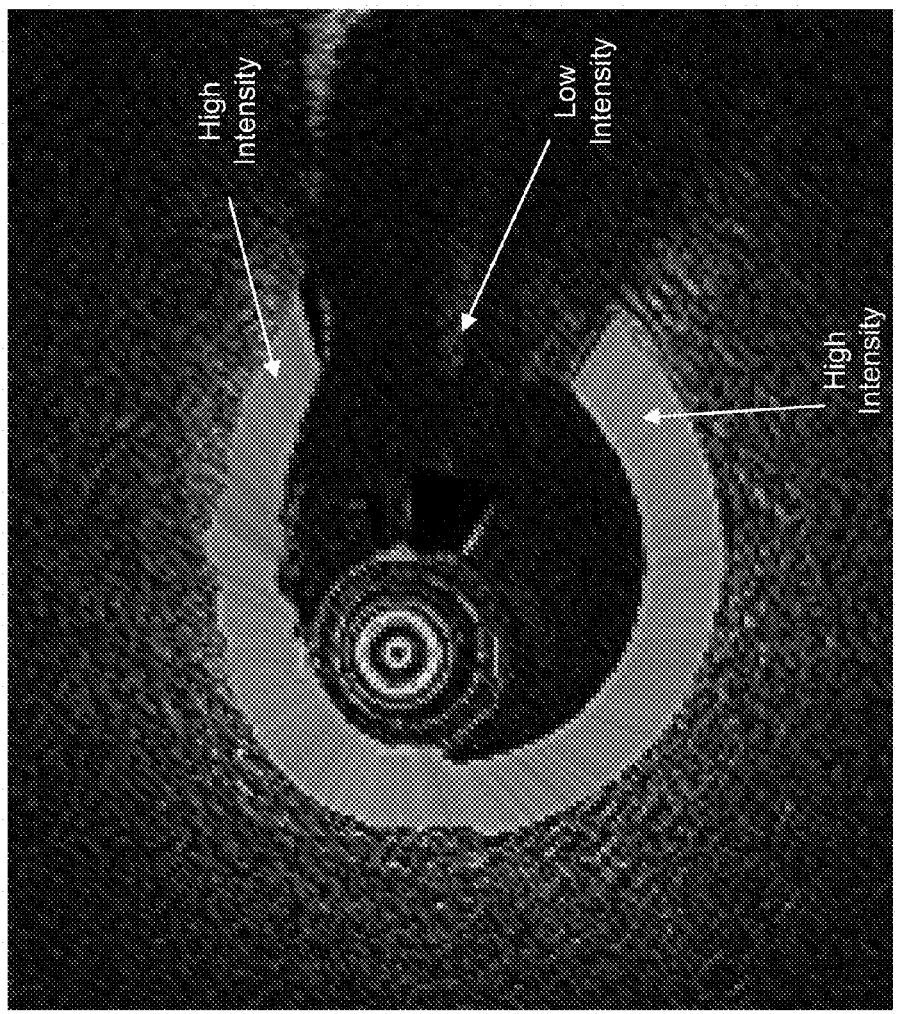

By applying the resulting cleared binary mask, such as shown in FIG. 5B, to the OCT image, the average intensity value along each scan line of the masked OCT image is calculated Step 2 as shown by the intensity band on the tissue region in FIG. 5C. From these intensity values, shadow regions are detected Step 3. Subject to the other techniques described herein, each shadow region can be a candidate or potential side branch. The potential side branch or shadow region is then evaluated via the use of a gradient operator applied to the intensity profile. The gradient operator (such as an edge or ridge detector) is configured to confirm the pattern of a high intensity region (end of vessel wall before side branch) that transitions to a low intensity region (shadow region of side branch), which again transitions back to a high intensity region (start of vessel wall after side branch). Once the candidate side branches are identified in phase 1 of the process of FIG. 4B, they are then evaluated using phase 2. In phase 2, a determination can be made as to whether a shadow region identified as a candidate side branch in phase 1 is or is more likely to be a side branch, blood in the imaging area, only a shadow, or something else. Once a final determination is made, the results can be output on a display, report or some other human or machine readable mechanism. Additional details relating to phase 2 are provided below. However, given the wide variation in side branch types and OCT imaging artifacts, it is useful to consider some of these points and how they are adjusted for before considering phase 2 which can use cross-frame data to improve detection accuracy.

Figure 6A:
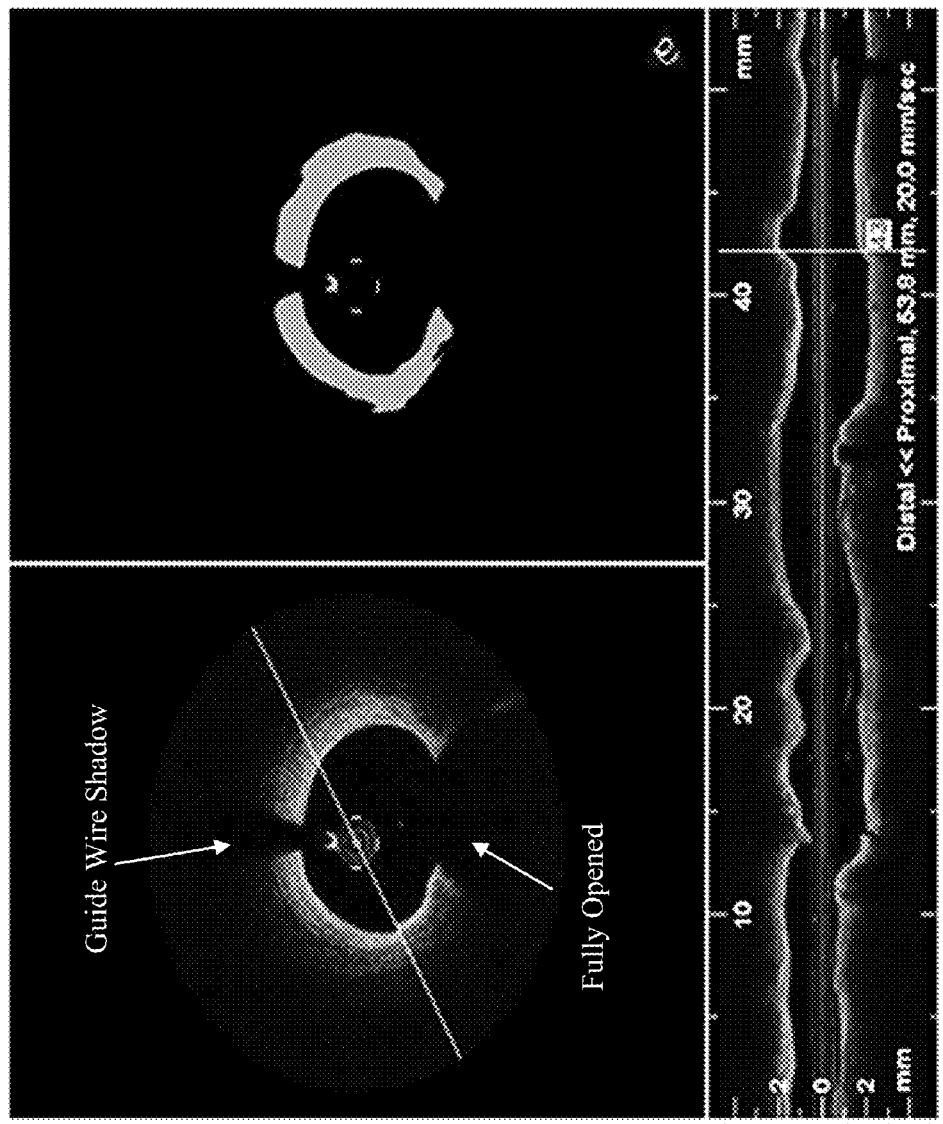
FIGS. 6A-6D show diagrams of side branches relative to image masks in each of a fully opened, partially opened, partially closed, or fully closed configuration in accordance with an illustrative embodiment of the invention.
Figure 6B:
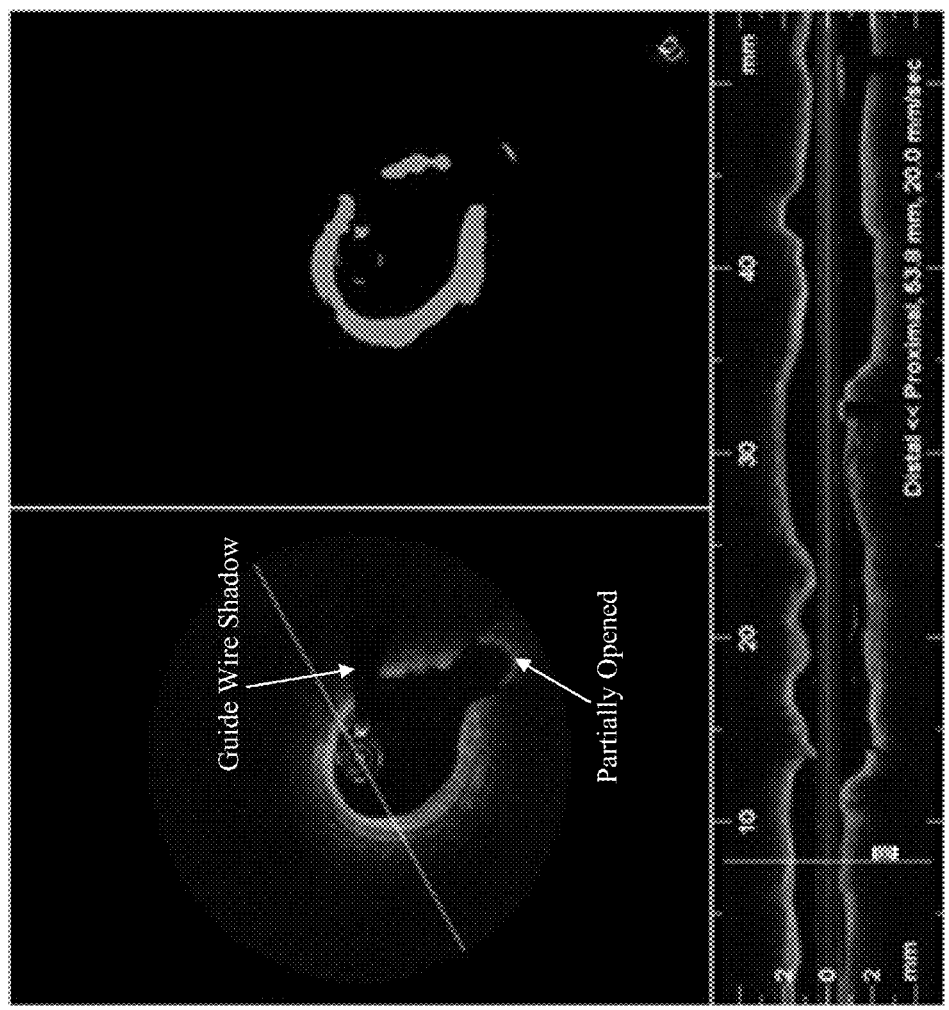
Figure 6C:
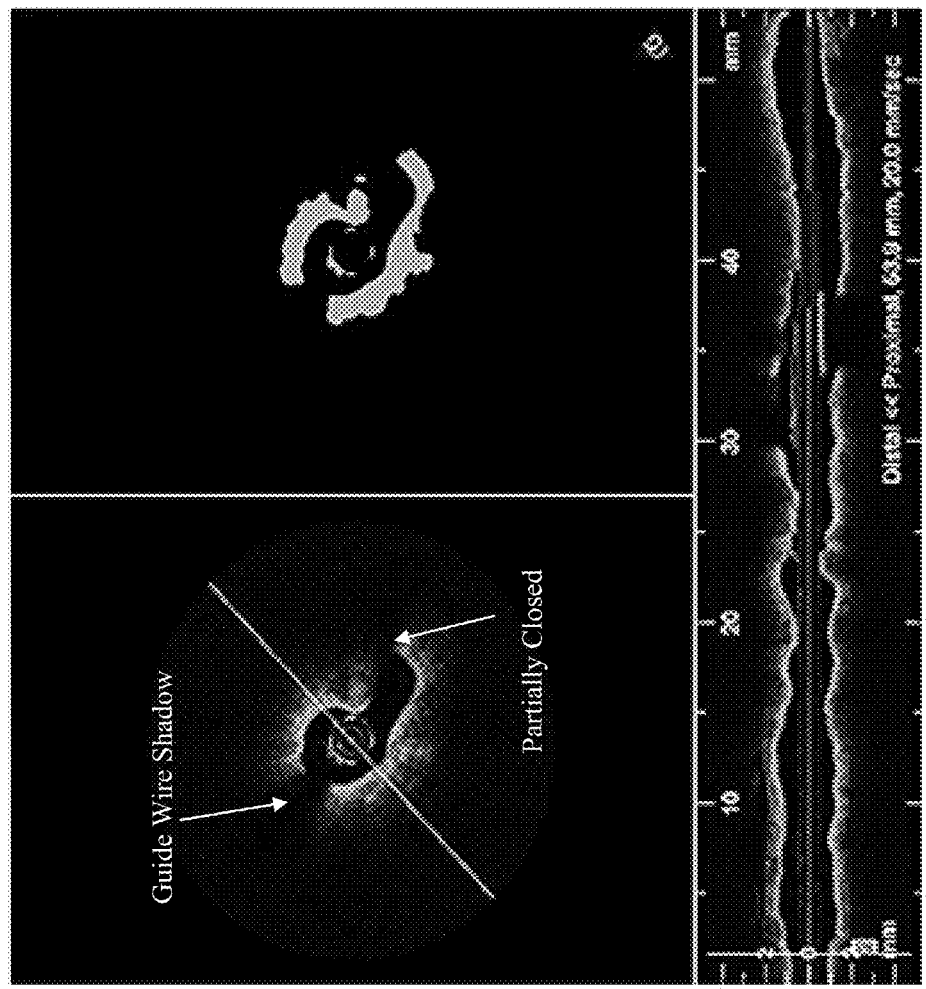
Figure 6D:
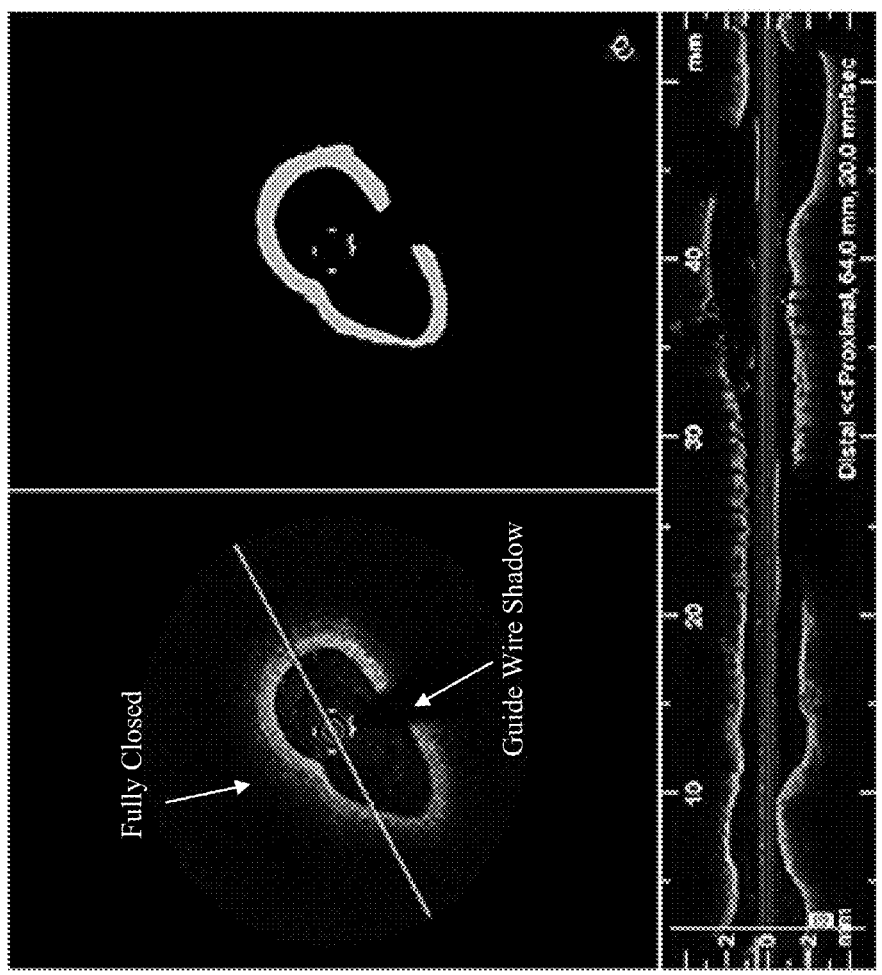

The application of the binary mask can have different outcomes depending on the side branch size and orientation. Generally, there are four side branch imaging scenarios or categories of side branches that can be obtained with respect to each frame or cross-section. FIGS. 6A-6D show a bottom L-mode view, an OCT cross-sectional image to the left and the associated binary image mask to the right. The side branch can appear in the mask as fully opened (FIG. 6A), partially opened (FIG. 6B), partially closed (FIG. 6C), or fully closed (FIG. 6D). In one embodiment, partially opened refers to the area of the opening of the side branch being less than the area of the side branch that is closed. In one embodiment, partially closed refers to the area of the opening of the side branch being greater than the area of the side branch that is closed. Thus, if the side branch appears more closed than open in an image it is partially open. If the side branch appears more open than closed, it is partially closed. These different views of a side branch can occur because as the OCT probe is pulled through the vessel the imaging beam emitted from the probe is generally at a right angle or another angle with respect to the longitudinal axis of the optical fiber. In addition, side branch openings have various geometries and as the fiber is pulled back, the OCT data collected can be scattered from different sections of the side branch. Once all of the data is collected during a pull back, the lower intensity regions of a side branch can appear as shown in FIGS. 6A-6D.

In order to detect the partially opened, partially closed, and fully closed side branches, a binary mask is also used. However, in one embodiment, the binary mask is modified by additional processing to modify the mask in these cases. One example of the additional processing used to modify the mask is to treat the side branch radius as an outlier to the mean radius of the image.

Figure 7:
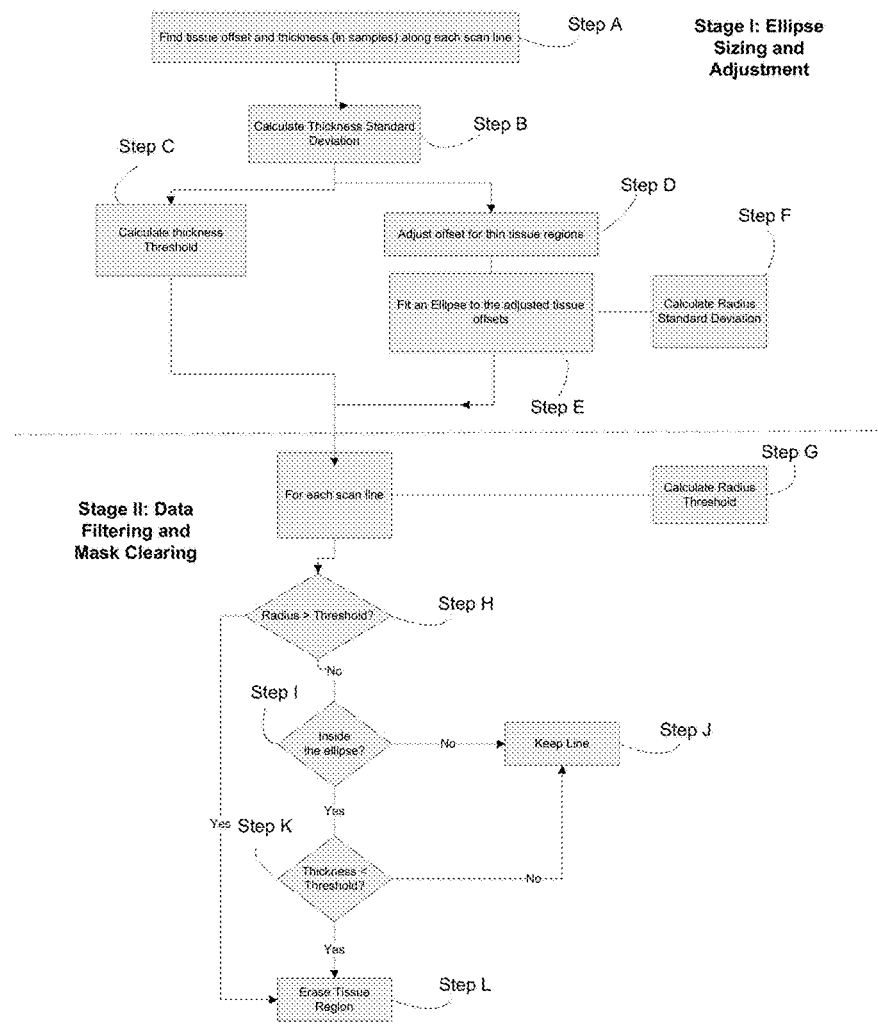
FIG. 7 shows an exemplary flow chart suitable for implementing a process to exclude foreground signals, such as signals from blood, from within the vessel in accordance with an illustrative embodiment of the invention.

As shown in FIG. 7, the side branch detection module is configured to evaluate the side branch radius and other data relative to a given vessel cross section. The method shown in FIG. 7 can be implemented in two stages. The first stage, Stage I, shown in the top half of the figure relates to sizing and placing an ellipse relative to a given vessel wall such that subsequent data filtering and clearing can be performed in the second stage, Stage II. The tissue thickness and offset position of the vessel wall can be calculated using the scan line data for each line Step A. The side branch radius refers to the distance measured from the center of the foreground into a side branch wall. In one embodiment of the invention, the center of the foreground can be obtained as the center of an ellipse fitted to the foreground. In another embodiment, the calculated centroid can be used as the center of the foreground.

The side branch radius is evaluated as an outlier relative to the mean radius of the OCT cross-sectional image. In one embodiment of the invention, this can be achieved by calculating the standard deviation of the radii calculated at each scan line Step B. A suitable threshold based on the calculated standard deviation can be determined Step C. This thickness threshold for the vessel wall can then be used to determine the outliers to the mean radius. If the vessel wall has thin regions, the ellipse is adjusted to be within these thin regions so as not to cut them off and accidentally create a side branch where none exist Step D. Given the data and offsets referenced herein, an ellipse can be properly fitted within a vessel without cutting off thin regions or other data of interest Step E. A threshold of the radii that should be within the vessel wall is determined in Step G using standard deviations of the radii determined in Step F. The outliers can be determined by detecting radii that fall outside the range of expected vessel radii, the threshold determined in Step G, based on the ellipse fitted relative to a given vessel cross-section in Step H. Thus, in Step H, if the radius suddenly changes relative to the other radii within the fitted ellipse, this is an indication of a partially open or a partially closed side branch for a given scan line or frame. This technique can be applied to individual cross sections as well as cross frames to detect regions of sudden abrupt changes to the radius of the vessel. These regions of abrupt radius changes are strong side branch discriminating features when the side branch is not fully opened and partially or fully visible. This approach is not typically used to detect areas that clearly show an opened side branch because the radius changes to a large value or is not detected.

Further, as shown in FIG. 7, if there is a change in radius indicative of an outlier and the relevant position of the data is within the ellipse Step I the data associated with this, such as the scan line is preserved and saved Step J. If blood is in the vessel and thus within the ellipse, it can cause a false positive reading as a tissue structure. However, blood lacks the thickness of tissue. Therefore, if an outlier is identified per the steps above, if the thickness threshold is not met by the thickness obtained with respect to the image data Step K, such as the blood, the associated data is erased or otherwise removed from the region within the ellipse Step L. If the thickness threshold is met, the data is likely to come from part of a side branch or another outlier instead of blood and the data is saved Step J.

Phase 2 of Side Branch Detection Embodiment

Once phase 1, one or more steps of phase 1, or other steps performed to generate candidate shadow regions fitting the high, low, high intensity pattern for a side branch are complete, the candidate side branches are subject to further processing or other factors are analyzed to evaluate the candidates. For example, low intensity regions from other sources such as stent struts, a guide wire and residual blood are also detected. Once detected, these can be screened and excluded as side branch candidates. As shown in FIG. 6A-6D, guide wire shadows are types of low intensity shadow regions that cannot be side branches, but have a similar appearance in OCT images. As a result, these need to be addressed as part of the image processing in some embodiments.

In phase 2, various steps can be performed to evaluate the side branch candidates identified in phase 1 as shown in Phase 2. These steps can include excluding guide wire regions Step 4, merging side branch regions Step 5, building a tree based on certain OCT data Step 6, pruning the tree Step 7, and interpolating gaps Step 8. These steps are discussed in more detail below. In one embodiment, one, all, or only a subset of these steps is performed. The first step to consider relates to guide wires and their associated shadow profile.

As noted above, one side effect of the inclusion of a guide wire as part of an OCT probe is its shadow. Unfortunately, it is easy for a side branch to be hidden in the shadow of a guide wire. Accordingly, in one embodiment, the first step in Phase 2 is to remove or exclude the guide wire regions Step 4. However, before it can be removed, it first needs to be processed for possible partial or total occlusion of side branches. One suitable guide wire detection algorithm is described in U.S. Pat. Publication No. 20110071404 filed on Sep. 22, 2010, the entire disclosure of which is incorporated by reference in its entirety. This process allows the software implementation of side branch detection module to reliably localize the guide wire.

Figure 8:
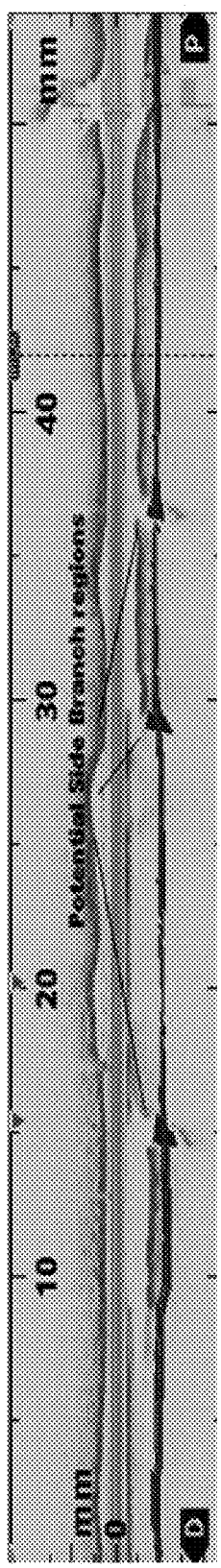
FIG. 8 shows a longitudinal cross-section of a vessel obtained using an OCT system having a guide wire shadow width profile showing potential side branch regions in accordance with an illustrative embodiment of the invention.

Increasing the reliability and sensitivity of the side branch detection algorithm can be achieved by performing one or more steps to detect side branches that are partially or fully occluded by guide wire shadow. In one embodiment of the invention this can be achieved by collecting and analyzing the width of the guide wire shadow. FIG. 8 shows an example of a guide wire shadow width profile. Typically, if a side branch is included in the guide wire shadow, the width can be considerably enlarged as a result of the shadow contribution from the guide wire and the side branch. This increase, such as the relative increase compared to a guide wire shadow alone, in shadow size can be detected. Therefore, by detecting regions in the image data that are consistent with such an increased guide wire shadow width profile the side branch detection module is able to identify guide wire shadow regions that are likely to include a side branch.

Using this information, the side branching detection module is configured to include guide wire regions that may include positive side branch detections. If the shadow profile of the guide wire region is not expected to overlap with or otherwise hide a side branch, it can be excluded. Again, detecting an enlargement in the guide wire shadow profile represents an enhancement to the detection process that reduces the risk that a side branch will go undetected. As an example, in FIG. 8 a guide wire shadow width profile showing three potential side branch regions is depicted.

The problem of removing outliers from the potential side branch detections can be formulated as finding the minimum spanning tree in a weighted graph. Outliers can include stents, shadows not associated with side branches, and other imaging artifacts. In a given pullback there can be multiple side branches and hence multiple trees each representing a side branch.

The midpoints of all detected shadow regions on all frames is collected and used as vertices of a graph which is a collection of one or more nodes which constitute the tree. The vertices of the graph are selected and connected to form a minimum spanning tree Step 6 such that: no points on the same frame are connected together; and any given vertex is connected to a parent vertex that minimizes a weight value. The weight value is calculated as the sum of the distance and slope difference between a vertex and its potential parent vertex. A new tree (for a potential separate side branch) is created when multiple vertices exist on the same frame or when a distance threshold is reached from the nearest potential parent. Due to blood and other artifacts, one large shadow region of a single side branch can appear as two adjacent smaller shadow regions. This situation can be detected and addressed before collecting midpoints of shadow regions. Step 5 is a merge step. This step compares potential shadow regions across frames and performs a conditional merge of adjacent shadow regions if it would minimize the angular difference across frames.

The resulting trees are then pruned Step 7 to remove outliers. The pruning is carried out as follows: any tree (side branch) less than two nodes or with a maximum width less than or equal to 0.5 mm is removed. The standard deviation of the angular position of the midpoint of the nodes of a given tree (side branch) is calculated and compared to a predetermined maximum angular standard deviation threshold. Any tree (side branch) that does not pass the test is considered an outlier and removed. Even when a side branch has been identified from the image data, there may be gaps in the data such as in the middle region of the side branch. The gaps (missed detections) in the middle of confirmed side branch detections can be interpolated to fill in data points to complete the continuation of a given side branch.

Non-Limiting Software Features and Embodiments for Implementing OCT Methods and Systems The following description is intended to provide an overview of device hardware and other operating components suitable for performing the methods of the invention described herein. This description is not intended to limit the applicable environments or the scope of the invention. Similarly, the hardware and other operating components may be suitable as part of the apparatuses described above. The invention can be practiced with other system configurations, including personal computers, multiprocessor systems, microprocessor-based or programmable electronic device, network PCs, minicomputers, mainframe computers, and the like. The invention can also be practiced in distributed computing environments where tasks are performed by remote processing devices that are linked through a communications network such as in different rooms of a catheter or cath lab.

Some portions of the detailed description are presented in terms of algorithms and symbolic representations of operations on data bits within a computer memory. These algorithmic descriptions and representations can be used by those skilled in the computer and software related fields. In one embodiment, a algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "calculating" or "comparing", "pruning," "generating" or "determining" or "displaying" Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The present invention, in some embodiments, also relates to apparatus for performing the operations herein. This apparatus may be specially constructed for the required purposes, or it may comprise a general purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language, and various embodiments may thus be implemented using a variety of programming languages.

Embodiments of the invention may be embodied in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present invention, some or all of the processing of the data collected using an OCT probe and the processor-based system is implemented as a set of computer program instructions that is converted into a computer executable form, stored as such in a computer readable medium, and executed by a microprocessor under the control of an operating system. Thus, query response and input data are transformed into processor understandable instructions suitable for generating OCT data, detecting side branches, detecting shadow regions, removing guide wire shadows, creating binary image masks, clearing binary image masks, comparing signals across different frames, performing signal to noise evaluation in images, and otherwise performing image comparison, signal processing, artifact removal, and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the Internet or World Wide Web).

Various examples of suitable processing modules are discussed below in more detail. As used herein a module refers to software, hardware, or firmware suitable for performing a specific data processing or data transmission task. Typically, in a preferred embodiment a module refers to a software routine, program, or other memory resident application suitable for receiving, transforming, routing and processing instructions, or various types of data such as OCT scan data, interferometer signal data, guide wire locations, shadow region locations, side branch locations, side branch diameters, intensity profiles, and other information of interest.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the invention described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the invention.

The aspects, embodiments, features, and examples of the invention are to be considered illustrative in all respects and are not intended to limit the invention, the scope of which is defined only by the claims. Other embodiments, modifications, and usages will be apparent to those skilled in the art without departing from the spirit and scope of the claimed invention.

The use of headings and sections in the application is not meant to limit the invention; each section can apply to any aspect, embodiment, or feature of the invention.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

What is claimed is:

1. A method of detecting a side branch for a vessel scanned using an imaging probe comprising:
   storing image data obtained during a pullback through the vessel in a memory device, the image data comprising a plurality of frames, each frame comprising a plurality of scan lines;
   identifying a first region having a first intensity in a first frame of the plurality of frames;
   identifying a second region having a second intensity in the first frame of the plurality of frames;
   identifying a third region having a third intensity in the first frame of the plurality of frames, wherein the first intensity is an average intensity of a first scan line, the second intensity is an average intensity of a second scan line, and the third intensity is an average intensity of a third scan line;
   comparing the first intensity to the second intensity;
   comparing the third intensity to the second intensity; and
   generating an output characterizing the second region as a candidate side branch when the first intensity and the third intensity are both greater than the second intensity.

2. The method of claim 1 wherein the second region has a first angular position and further comprising the step of determining if a shadow region having a second angular position the same as the first angular position is present in a second frame adjacent to the first frame.

3. The method of claim 1 wherein the first intensity and the third intensity are substantially equal.

4. The method of claim 1 wherein the first region and the third region are separated by a gap which at least partially defines the second region.

5. The method of claim 1 further comprising the step of applying a binary image mask such that each of the first intensity, the second intensity, and the third intensity are characterized as foreground data or background data in response to their respective intensities.

6. The method of claim 1 further comprising the step of fitting an ellipse between at least two of the first, second, and third regions and excluding at least one additional region disposed in the ellipse having a fourth intensity greater than the second intensity.

7. The method of claim 1 wherein the image data is optical coherence tomography image data and further comprising the step of determining if the second region is a side branch using optical coherence tomography image data from one or more adjacent frames.

8. The method of claim 1 further comprising the step of detecting a guide wire in the first frame and determining that the second region is a side branch if the guide wire has a shadow profile that exceeds a predetermined shadow profile threshold.

9. The method of claim 1 further comprising the steps of building a computer-based tree using a plurality of midpoints of detected shadow regions and pruning the tree to determine if the second region is an outlier or a side branch.

10. The method of claim 9 wherein the outlier is selected from the group consisting of a shadow, blood, thin tissue, a stent, and an imaging artifact.

11. The method of claim 1 wherein the image data is optical coherence tomography image data and the imaging probe is an optical coherence tomography probe.

12. A method of detecting a side branch for a vessel scanned using an imaging probe comprising:

storing image data obtained during a pullback through the vessel in a memory device, the image data comprising a plurality of frames;

identifying a first region having a first intensity in a first frame of the plurality of frames;

identifying a second region having a second intensity in the first frame of the plurality of frames, wherein the second region has a first angular position;

identifying a shadow region having a second angular position in a second frame adjacent to the first frame; and generating an output characterizing the second region as a candidate side branch when the first intensity is greater than the second intensity and when the second angular position is the same as the first angular position.

13. The method of claim 12 wherein the first intensity and the third intensity are substantially equal.

14. The method of claim 12 wherein the first region and the third region are separated by a gap which at least partially defines the second region.

15. The method of claim 12 further comprising the step of applying a binary image mask such that each of the first intensity, the second intensity, and the third intensity are characterized as foreground data or background data in response to their respective intensities.

16. The method of claim 12 further comprising the step of fitting an ellipse between at least two of the first, second, and third regions and excluding at least one additional region disposed in the ellipse having a fourth intensity greater than the second intensity.

17. The method of claim 12 wherein the image data is optical coherence tomography image data and further comprising the step of determining if the second region is a side branch using optical coherence tomography image data from one or more adjacent frames.

18. The method of claim 12 further comprising the step of detecting a guide wire in the first frame and determining that the second region is a side branch if the guide wire has a shadow profile that exceeds a predetermined shadow profile threshold.

19. The method of claim 12 further comprising the steps of building a computer-based tree using a plurality of midpoints of detected shadow regions and pruning the tree to determine if the second region is an outlier or a side branch.

20. The method of claim 19 wherein the outlier is selected from the group consisting of a shadow, blood, thin tissue, a stent, and an imaging artifact.

21. The method of claim 12 wherein the image data is optical coherence tomography image data and the imaging probe is an optical coherence tomography probe.

* * * * *